United States Patent [19]

Marxer

[11] 4,292,429
[45] Sep. 29, 1981

[54] IMIDAZOLE UREA AND AMIDO COMPOUNDS

[75] Inventor: Adrian Marxer, Muttenz, Switzerland

[73] Assignee: Ciba-Geigy Corporation, Ardsley, N.Y.

[21] Appl. No.: 14,661

[22] Filed: Feb. 23, 1979

[30] Foreign Application Priority Data

Mar. 8, 1978 [CH] Switzerland .................. 2519/78

[51] Int. Cl.³ .................. C07D 401/04; C07D 401/06; C07D 401/12
[52] U.S. Cl. ..................... 546/278; 544/332; 544/333; 546/256; 548/315; 548/316; 548/348; 548/352; 548/353; 424/251; 424/263; 424/273 R
[58] Field of Search .................. 546/278; 424/263

[56] References Cited

U.S. PATENT DOCUMENTS 3,359,274 12/1967 Billinghurst ...................... 546/278
4,088,766 5/1978 Callahan et al. ................... 424/263
4,112,100 9/1978 Callahan et al. ................... 424/263

*Primary Examiner*—Henry R. Jiles
*Assistant Examiner*—Natalia Harkaway
*Attorney, Agent, or Firm*—Prabodh I. Almaula

[57] ABSTRACT

The invention relates to urea and amido compounds of the formula

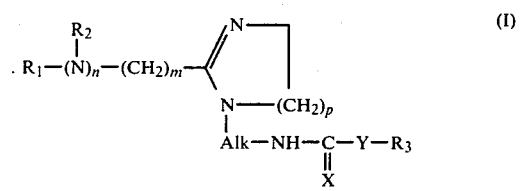

which have a powerful action on tumors, and to processes for their preparation and pharmaceutical preparations containing such compounds.

6 Claims, No Drawings

IMIDAZOLE UREA AND AMIDO COMPOUNDS

The present invention relates to a process for the preparation of novel urea and amido compounds of the formula

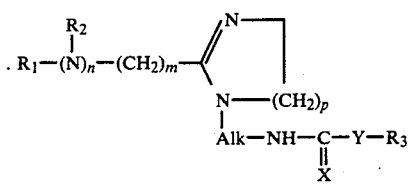

(I)

in which $R_1$ and $R_3$ are a monocyclic, carbocyclic aryl or hetero-aryl, n is 0 or 1, m is 0, 1 or 2, p is 1 or 2, $R_2$ is a hydrogen atom or lower alkyl, Alk is a lower alkylene group having 2–3 carbon atoms in the linear chain, X is oxygen or sulfur and Y is an imino group or a direct bond, and their salts.

In this specification, lower radicals are, in particular, those radicals which contain not more than 7 C atoms and especially not more than 4 C atoms.

A monocyclic, carbocyclic aryl radical is a substituted or unsubstituted phenyl radical, for example a monosubstituted, disubstituted or polysubstituted phenyl radical or an unsubstituted phenyl radical.

A heteroaryl radical is in particular a substituted or unsubstituted monoazacyclic or diazacyclic 6-membered radical or monothiacyclic radical of aromatic character, which, for example, in the same way as the monocyclic, carbocyclic aryl radical can be, for example, monosubstituted, disubstituted or polysubstituted. A heteroaryl radical is a substituted or unsubstituted pyridyl, pyrimidinyl or thienyl radical, for example a monosubstituted, disubstituted or polysubstituted 2-pyridyl, 4-pyridyl, 2-pyrimidinyl or 4-pyrimidinyl or 2-thienyl or 3-thienyl radical.

Lower alkyl radicals are, for example, methyl, ethyl, n-propyl or isopropyl, or straight-chain or branched butyl, pentyl, hexyl or heptyl and these can be bonded in any position.

Lower alkylene is a branched or in particular straight-chain lower alkylene having 2–3 C atoms in the alkylene chain, such as 1,2-propylene, 1,3-propylene, 1,2-butylene, 2,3-butylene, 1,3-butylene or especially 1,2-ethylene.

If a phenyl radical or pyridyl, pyrimidinyl or thienyl radical $R_1$ or $R_3$ is monosubstituted or polysubstituted, the substituents can be, for example, lower alkyl, halogen, trifluoromethyl, lower alkoxy, carboxyl or lower alkoxycarbonyl.

A phenyl, pyridyl, pyrimidinyl or thienyl radical can, for example, be substituted by the lower alkyl groups defined above or by the lower alkoxy or lower alkoxycarbonyl groups defined further below or by halogen or a trifluoromethyl group or carboxyl group.

Halogen atoms are halogen atoms with an atomic number of not more than 35, for example fluorine, chlorine or bromine.

Lower alkoxy is, for example, methoxy, ethoxy, n-propoxy, isopropoxy, n-butoxy or n-pentyloxy or n-hexyloxy. Lower alkoxycarbonyl is, for example, methoxy-, ethoxy-, n-propoxy- or isopropoxy-carbonyl or straight-chain or branched butoxy-, pentyloxy-, hexyloxy- or heptyloxy-carbonyl, which in the lower alkyl radical can be bonded in any position. The novel compounds have valuable pharmacological properties and in particular they have a powerful action against tumours, for example against epidermoid carcinomas induced by diethylnitrosamine (DAENA) in the lungs, the trachea and the larynx in Syrian golden hamsters or against the Ehrlich ascites carcinoma in mice.

Thus, the treatment of golden hamsters with respiratory carcinomas (from week 10 after DAENA) with compounds such as 1-[2-[2-(2-chlorophenyl)-2-imidazolin-1-yl]-ethyl]-3-(p-tolyl)-urea or 1-[2-[2-(4-pyridyl)-2-imidazolin-1-yl]-ethyl]-3-(4-carboxy-phenyl)-urea in doses of 12.5–100 mg/kg administered perorally, administration being 5 times per week for 4 weeks, effected a dosage-dependent reduction of up to 90% in the number of epidermoid carcinomas in the lung, compared with controls. The treatment with, for example, 50 mg/kg administered perorally showed a highly significant difference ($P \leq 0.001$) compared with the controls. The inhibition of tumour growth in the larynx and the trachea was 65 and 66% respectively. The compounds are therefore therapeutically particularly valuable in the case of bronchial carcinomas which are not influenced by current cytostatic agents. The Ehrlich ascites carcinoma is extensively inhibited by some of these compounds, for example by 1-[2-[2-(chloroanilinomethyl)-2-imidazolin-1-yl]-ethyl]-3-(p-tolyl)-urea. The tolerance is good. No side effects or macroscopically visible changes in the organs are found even after 4 weeks treatment. Likewise, there is no cumulative toxicity when the treatment is repeated daily, compared with a single administration.

The invention relates in particular to compounds of the formula I in which $R_1$ and $R_3$ are a monocyclic, carbocyclic aryl or hetero-aryl, n is 0 or 1, m is 0, 1 or 2 and p is 1 or 2, with the proviso that if m is 0 n is 0, $R_2$ is a hydrogen atom or lower alkyl, Alk is a lower alkylene group having 2–3 carbon atoms in the linear chain, X is oxygen or sulfur and Y is an imino group or a direct bond, and their salts.

The invention relates especially to those compounds of the formula I in which $R_1$ and $R_3$ are a substituted or unsubstituted phenyl or pyridyl, n is 0 or 1, m is 0, 1 or 2 and p is 1, with the proviso that if m is 0 n is 0, $R_2$ is a hydrogen atom, Alk is a lower alkylene group having 2 carbon atoms in the linear chain, X is oxygen or sulfur and Y is an imino group or a direct bond, and their salts.

Compounds of the formula I which are of particular interest are those in which $R_1$ and $R_3$ are a phenyl or pyridyl which is unsubstituted or substituted by halogen, lower alkyl, carboxyl or trifluoromethyl, n is 0 or 1, m is 0 or 1 and p is 1, with the proviso that if m is 0 n is 0, $R_2$ is a hydrogen atom, Alk is a lower alkylene group having 2 carbon atoms in the linear chain, X is oxygen and Y is an imino group or a direct bond, and their salts.

Compounds of the formula I which are of very particular interest are those in which $R_1$ is a phenyl or 2- or 4-pyridyl which is unsubstituted or substituted by chlorine, methyl, carboxyl or trifluoromethyl, n is 0 or 1, m is 0 or 1 and p is 1, with the proviso that if m is 0 n is 0, $R_2$ is a hydrogen atom, Alk is a 1,2-ethylene group, X is oxygen and Y is an imino group, and their salts.

Amongst these novel compounds of the formula I, particularly preferred compounds are those described in the examples.

Compounds of the general formula I are prepared by reacting compounds of the general formula II

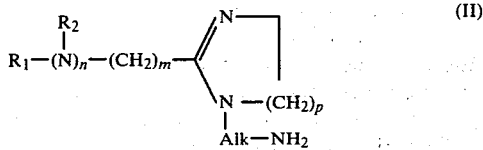

in which $R_1$, $R_2$, n, m, p and Alk are as defined above, with a reactive derivative of the acid of the general formula III

in which X, Y and $R_3$ are as defined above, and, if desired, converting a resulting compound of the general formula I into an acid addition salt.

Reactive derivatives of the acid of the general formula III, in which Y is an imino group, which can be used for the reaction are inner anhydrides, i.e. isocyanates or thioisocyanates of the general formula IV

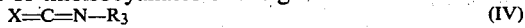

in which X and $R_3$ are as defined above. The reactions are carried out in a temperature range between 0° and 140° C., but preferably at a temperature between 20° and 90° C., in the presence of a solvent, for example a lower alkanol or ester, for example ethyl acetate, an ether, for example tetrahydrofuran, a ketone, for example ethyl methyl ketone, or an aromatic hydrocarbon, for example benzene, toluene or xylene.

Further reactive derivatives of the acid of the general formula III which can be used for the reaction are halides of the carbamic acid or thiocarbamic acid of the general formula V

in which X and $R_3$ are as defined above and Hal is a halogen atom. The reactions can be carried out in a manner analogous to that used in the case of the isocyanates and thioisocyanates, in the same temperature range and using an analogous solvent, and in the presence or absence of a trialkylamine, for example triethylamine, $K_2CO_3$ and the like as an acid-binding agent.

Further reactive derivatives of the acid of the general formula III which can be used are halides of $R_3$-carboxylic acids of the general formula Va

in which $R_3$ is as defined above.

The compounds of the formula II which are used as starting materials are known and can be obtained by reacting a substituted or unsubstituted anilinomethylnitrile, arylmethylnitrile or arylnitrile, or the corresponding heteroaryl compounds of the formula VI

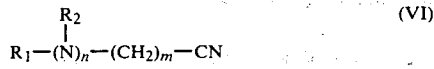

with the corresponding diethylene- or dipropylene-triamine (A. Marxer, J.A. Chem. Soc. 79, 467 (1957)).

The substituted or unsubstituted anilinomethylnitriles and the corresponding heteroaryl compounds of the formula VI which are used are also known and are obtained from the corresponding aniline compounds or heteroaryl compounds by reaction with formaldehyde and hydrogen cyanide (A. Marxer, Helv. Chim. Acta 37, 166 (1954)).

Compounds of the general formula I in which $R_1$, $R_2$, $R_3$, X, Y, n, m and p are as defined above can also be prepared in the same way as the starting materials of the general formula II, by reacting a compound of the general formula VI

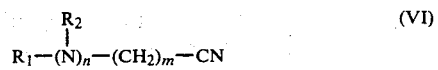

with a diethylene- or dipropylene-triamine derivative of the general formula VII

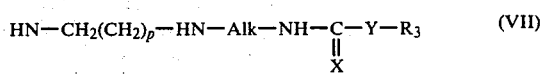

(A. Marxer, J.A. Chem. Soc. 79, 467 (1957)).

Compounds of the general formula I in which $R_3$ is substituted by a lower alkoxycarbonyl group, for example by an ethoxycarbonyl group, can be converted by saponification, i.e. by hydrolysis in an acid or alkaline medium, to compounds of the formula I in which $R_3$ is, for example, a phenyl radical substituted by a carboxyl group. The hydrolysis is preferably carried out in an alkaline medium, i.e. in the presence of a strong alkali metal or alkaline earth metal base, for example sodium hydroxide solution.

Depending on the process conditions and the starting materials, the end products are obtained in the free form or in the form of their acid addition salts, which also are included in the invention. Thus, for example, basic, neutral or mixed salts and in some cases also hemihydrates, monohydrates, sesquihydrates or polyhydrates thereof, can be obtained. The acid addition salts of the novel compounds can be converted to the free compound in a manner known per se, for example using basic agents, such as alkalis or ion exchangers. On the other hand, the resulting free bases can form salts with organic or inorganic acids. The acids used to prepare acid addition salts are in particular those which are suitable for forming therapeutically acceptable salts. Examples of such acids are: hydrogen halide acids, sulfuric acids, phosphoric acids, nitric acid, aliphatic, alicyclic, aromatic or heterocyclic carboxylic or sulfonic acids, such as formic acid, acetic acid, propionic acid, succinic acid, glycollic acid, lactic acid, malic acid, tartaric acid, citric acid, ascorbic acid, maleic acid, hydroxymaleic acid or pyruvic acid; phenylacetic acid, benzoic acid, p-aminobenzoic acid, anthranilic acid, p-hydroxybenzoic acid, salicyclic acid or p-aminosalicylic acid, embonic acid, methanesulfonic acid, ethanesulfonic acid, hydroxyethanesulfonic acid and ethylenesulfonic acid; a halogenobenzenesulfonic acid, toluenesulfonic acid, naphthalenesulfonic acid or sulfanilic acid; or methionine, tryptophane, lysine or arginine.

These or other salts of the novel compounds, for example the picrates, can also be used to purify the resulting free bases, by converting the free bases to salts, separating off the salts and liberating the bases from the salts again. Because of the close relationships between the novel compounds in the free form and in the form of their salts, what is stated in this specification in respect of the free compounds also applies by analogy to the corresponding salts.

Depending on the number of asymmetric C atoms and on the choice of starting materials and procedures, the novel compounds can be in the form of mixtures of racemates, racemates or optical antipodes.

Mixtures of racemates can be separated into the pure racemates in a known manner on the basis of the physico-chemical differences between the constituents, for example by chromatography and/or fractional crystallisation.

Pure racemates can be resolved by known methods, for example by recrystallisation from an optically active solvent, with the aid of micro-organisms, or by reaction with an optically active acid which forms salts with the racemic compound and separation of the salts obtained in this way, for example on the basis of their different solubilities, into the diastereomers, from which the antipodes can be liberated by the action of suitable agents. Optically active acids particularly commonly used are, for example, the D and L forms of tartaric acid, di-o-toluyltartaric acid, malic acid, mandelic acid, camphorsulfonic acid or quinic acid. Advantageously, the more active of the two antipodes is isolated.

According to the invention, however, the end products can also be obtained in the form of the pure racemates or optical antipodes by using starting materials which contain one or more asymmetric C atoms in the form of the pure racemates or optical antipodes.

The novel active compounds or the pharmaceutically acceptable salts can be administered enterally, such as orally or rectally, and also parenterally.

The pharmaceutical compositions of matter according to the invention contain at least one compound of the general formula I (see above) as the active ingredient, together with a conventional pharmaceutical carrier. The nature of the carriers depends largely on the field of application.

Suitable preparations for the oral treatment of tumours are, in particular, solid dosage unit forms, such as tablets, sugar-coated tablets and capsules. The daily doses are between 8 and 100 mg/kg for warm-blooded animals. Suitable dosage unit forms such as sugar-coated tablets or tablets preferably contain 10–200 mg of an active compound according to the invention, the active ingredient content being 10–90 percent by weight. In order to prepare tablets and sugar-coated tablet cores, the compounds of the general formula I are combined with solid, pulverulent carriers, such as lactose, sucrose, sorbitol, corn starch, potato starch or amylopectin, cellulose derivatives or gelatin, preferably with the addition of lubricants, such as magnesium stearate or calcium stearate or polyethylene glycols of suitable molecular weight. Sugar-coated tablet cores are subsequently coated, for example with concentrated sugar solutions, which, for example, can also contain gum arabic, talc and/or titanium dioxide, or with a Shellack dissolved in mixtures of readily volatile organic solvents. Dyes can be added to these coatings, for example to indicate different doses of active ingredient. Soft gelatin capsules and other sealed capsules consist, for example, of a mixture of gelatin and glycerin and can contain, for example, mixtures of a compound of the formula I with polyethylene glycol. Dry-filled capsules contain, for example, granules of an active ingredient with solid, pulverulent carriers, for example lactose, sucrose, sorbitol or mannitol; starches, such as potato starch, corn starch or amylopectin, cellulose derivatives and gelatin and also magnesium stearate or stearic acid.

The following examples (a) to (d) illustrate the preparation of some typical administration forms but do not in any way represent the sole embodiments of such administration forms.

(a) 250.0 g of the active ingredient are mixed with 550.0 g of lactose and 292.0 g of potato starch and the mixture is moistened with an alcoholic solution of 8 g of gelatin and granulated through a sieve. After drying, 60.0 g of potato starch, 60.0 g of talc, 10.0 g of magnesium stearate and 20.0 g of colloidal silica are mixed in and the mixture is compressed to 10,000 tablets each weighing 125 mg and containing 25 mg of active ingredient; if desired, these tablets can be provided with breaking notches for finer adjustment of the dosage.

(b) Granules are prepared from 100.0 g of active ingredient, 379.0 g of lactose and an alcoholic solution of 6.0 g of gelatin and, after drying, these granules are mixed with 10.0 g of colloidal silica, 40.0 g of talc, 60.0 g of potato starch and 5.0 g of magnesium stearate and the mixture is compressed to 10,000 sugar-coated tablet cores. These cores are then coated with a concentrated syrup of 533.5 g of crystalline sucrose, 20.0 g of Shellack, 75.0 g of gum arabic, 250.0 g of talc, 20.0 g of colliodal silica and 1.5 g of dye and dried. The resulting sugar-coated tablets each weigh 150 mg and each contain 10 mg of active ingredient.

(c) In order to prepare a syrup with an active ingredient content of 0.25%, 1.5 liters of glycerin, 42 g of methyl p-hydroxybenzoate, 18 g of n-propyl p-hydroxybenzoate and, with slight warming, 25.0 g of active ingredient are dissolved in 3 liters of distilled water, 4 liters of 70% sorbitol solution, 1,000 g of crystalline sucrose, 350 g of glucose and an aroma substance, for example 250 g of "Orange Peel Soluble Fluid" from Eli Lilly and Col, Indianapolis, or 5 g of natural lemon aroma and 5 g of "half and half" essence, both obtainable from Haarmann and Reimer, Holzminden, Germany, are added, the resulting solution is filtered and the filtrate is made up to 10 liters with distilled water.

(d) In order to prepare 1,000 capsules each containing 100 mg of active ingredient, 100 g of active ingredient are mixed with 173.0 g of lactose and the mixture is uniformly moistened with an aqueous solution of 2.0 g of gelatin and granulated through a suitable sieve (for example sieve III according to Ph.Helv. V). The granules are mixed with 10.0 g of dried corn starch and 15.0 g of talc and the mixture is filled in uniform amounts into 1,000 size 1 hard gelatin capsules.

(e) Pharmaceutical preparations for rectal use are, for example, suppositories, which consist of a combination of a compound of the general formula I, as the active ingredient, with a suppository base. Examples of suitable suppository bases are natural or synthetic triglycerides, paraffin hydrocarbons, polyethylene glycols or higher alkanols. Furthermore, gelatin rectal capsules, which consist of a combination of the active ingredient with a base, can also be used; suitable base materials are, for example, liquid triglycerides, polyethylene glycols or paraffin hydrocarbons.

(f) Preparations suitable for parenteral administration are, in particular, injection solutions of the salts described above. Injection solutions of a hydrochloride are prepared, for example, as follows: 20.0 g of the hydrochloride of an active ingredient are dissolved in 1,500 ml of thoroughly boiled, pyrogen-free water and the solution is made up to 2,000 ml with the same type of water. The solution is filtered and the filtrate is filled into 1,000 2 ml ampoules and sterilised. One 2 ml ampoule contains 20 mg or 1.0% of active ingredient.

The following examples illustrate the preparation of the novel compounds of the general formula I, and of intermediates which have not been described hitherto, in more detail but are not in any way the sole embodiments of these. The temperatures are in degrees centigrade.

EXAMPLE 1

(a) 54.3 g of 1-aminoethyl-2-(2,6-dichloroanilinomethyl)-2-imidazoline are dissolved in 300 ml of absolute toluene and, at room temperature, 25.2 g of p-tolyl isocyanate in 100 ml of toluene are added dropwise, the mixture warming to about 33° during the addition. The mixture is then stirred for 3 hours at a temperature of 90°, a small amount of crystalline turbidity is filtered off and the reaction mixture is concentrated to half its volume. After grinding, 1-[2-[2-(2,6-dichloroanilinomethyl)-2-imidazolin-1-yl]-ethyl]-3-(p-tolyl)-urea with a melting point of 94°-97° crystallises out.

The maleate is obtained by dissolving 57.0 g of the urea obtained above in 250 ml of acetone and adding a solution of 15.8 g of maleic acid in 100 ml of acetone. After leaving to stand for a relatively short time, 1-[2-[2-(2,6-dichloroanilinomethyl)-2-imidazolin-yl]-ethyl]-3-(p-tolyl)-urea maleate crystallises out and after filtering off with suction and washing thoroughly this melts at a temperature of 185°-187° with decomposition.

(b) The starting material required for the preparation, i.e. 1-aminoethyl-2-(2,6-dichloroanilinomethyl)-2-imidazoline, is prepared as follows:

60.4 g of 2,6-dichloroanilinoacetonitrile and 34.0 g of diethylenetriamine are heated in the presence of 250 mg of hydrogen sulfide gas until the evolution of ammonia has ceased. For purification, the resulting free base, i.e. 1-aminoethyl-2-(2,6-dichloroanilinomethyl)-2-imidazoline, is dissolved in ethyl acetate and 2.5 N alcoholic hydrochloric acid is added and the base is thus converted to the dihydrochloride which has a melting point of 254°-258°. The purified base is prepared from the dihydrochloride by dissolving in water and precipitating with 10 N sodium hydroxide solution and subsequently extracting with ether.

EXAMPLE 2

(a) 13.3 g of p-tolyl isocyanate in 50 ml of absolute toluene are added dropwise to 22.4 g of 1-aminoethyl-2-(2-chlorophenyl)-2-imidazoline dissolved in 125 ml of absolute toluene, with ice water-cooling. The reaction mixture, which has warmed as a result of the exothermic reaction, is stirred for 3 hours at a temperature of 90° and an oily substance separates out. The toluene used as the solvent is evaporated off and the residue is combined with the oil which has separated out; this crystallises on leaving to stand for some time. The resulting crystalline product is suspended in 200 ml of warm ethyl acetate and the suspension is boiled briefly. 1-[2-[2-(2-Chlorophenyl)-2-imidazolin-1-yl[-ethyl]-3-(p-tolyl)-urea, which is thus isolated as insoluble matter, melts at 166°-167°. The hydrochloride is obtained by suspending 57.0 g of the urea obtained above in 100 ml of ethyl acetate, adding 77.5 ml of 2.08 N alcoholic hydrochloric acid, filtering the resulting solution and adding a further 100 ml of ethyl acetate to the filtrate. 1-[2-[2-(2-Chlorophenyl)-2-imidazolin-1-yl]-ethyl]-3-(p-tolyl)-urea hydrochloride, which has separated out as crystals, melts at 108°-111° (contains about 1 mol of water of crystallisation).

(b) The starting material required for the reaction, i.e. 1-aminoethyl-2-(2-chlorophenyl)-2-imidazoline, is prepared in a manner analogous to that described under 1 (b), using 68.8 g of 2-chlorobenzonitrile, 57.9 g of diethylenetriamine and 300 mg of hydrogen sulfide gas; boiling point 154°/0.02 mm Hg.

EXAMPLE 3

(a) 1-[2-[2-(Anilinomethyl)-2-imidazolin-1-yl]-ethyl]-3-(p-tolyl)-urea is prepared from 21.8 g of 1-aminoethyl-2-(anilinomethyl)-2-imidazoline and 13.3 g of p-tolyl isocyanate in a manner analogous to that described under 2 (a); after recrystallisation from ethyl acetate and ethanol, this product melts at a temperature of 159°-161°. The maleate prepared by the process described under 2 (a) melts at a temperature of 104°-106°. Depending on the moisture content, the temperature rises up to 115°-118°.

(b) Before purification, the 1-aminoethyl-2-(anilinomethyl)-2-imidazoline obtained from anilinoacetonitrile and diethylenetriamine by the process described under 1 (b) melts, after conversion to the dihydrochloride, at a temperature of 106° with decomposition. For the reaction, the free base is prepared from the dihydrochloride by dissolving in water and precipitating with 10 N sodium hydroxide solution.

EXAMPLE 4

1-[2-[2-(2,6-Dichloroanilinomethyl)-2-imidazolin-1-yl]-ethyl]-3-(phenyl)-urea is obtained from 21.1 g of 1-aminoethyl-2-(2,6-dichloroanilinomethyl)-2-imidazoline and 8.8 g of phenyl isocyanate in a manner analogous to that described under 2 (a); the product is obtained as an oil and after converting to the maleate in a mixture of acetone and ethyl acetate is obtained as crystals. Melting point 163°-165° with decomposition.

EXAMPLE 5

(a) 1-[2-[2-(2-Chloroanilinomethyl)-2-imidazolin-1-yl]-ethyl]-3-(3-trifluoromethylphenyl)-urea is obtained from 25.2 g of 1-aminoethyl-2-(2-chloroanilinomethyl)-2-imidazoline and 18.7 g of m-trifluoromethyl-phenyl isocyanate in a manner analogous to that described under 2 (a) and after suspending in ethyl acetate this product melts at a temperature of 181°-183°. The hydrochloride prepared therefrom melts at a temperature of 107° and the water of crystallisation is removed on drying under a high vacuum.

(b) 1-Aminoethyl-2-(2-chloroanilinomethyl)-2-imidazoline, which is obtained from o-chloroanilinoacetonitrile and diethylenetriamine by the process described under 1 (b), is purified via the corresponding oxalate.

EXAMPLE 6

(a) 1-[2-[2-(4-Chloroanilinomethyl)-2-imidazolin-1-yl]-ethyl]-3-(4-trifluoromethylphenyl)-urea with a melting point of 173°-177° is obtained from 25.3 g of 1-aminoethyl-2-(4-chloroanilinomethyl)-2-imidazoline and 18.7 g of p-trifluoromethylphenyl isocyanate in a manner analogous to that described under 2 (a); after converting to the hydrochloride, this product melts at a temperature of 170°-172°.

(b) 1-Aminoethyl-2-(4-chloroanilinomethyl)-2-imidazoline, which is obtained from p-chloroanilinoacetonitrile and diethylenetriamine by the process described under 1 (b), melts, in the form of the dihydrochloride, at a temperature of 204°. The base is obtained therefrom in the form of an oil.

EXAMPLE 7

1-[2-[2-(2-Chloroanilinomethyl)-2-imidazolin-1-yl]-ethyl]-3-(p-tolyl)-urea with a melting point of 142°–144° is obtained from 25.3 g of 1-aminoethyl-2-(2-chloroanilinomethyl)-2-imidazoline and 13.3 g of p-tolyl isocyanate in a manner analogous to that described under 1 (a). The maleate prepared by the process described under 1 (a) melts at a temperature of 126°–127°.

EXAMPLE 8

1-[2-[2-(Anilinomethyl)-2-imidazolin-1-yl]-ethyl]-3-(3-chlorophenyl)-urea with a melting point of 140°–143° is obtained from 21.8 g of 1-aminoethyl-2-(anilinomethyl)-2-imidazoline and 15.4 g of m-chlorophenyl isocyanate in a manner analogous to that described under 1 (a). The maleate prepared by the process described under 1 (a) melts at a temperature of 111°–113°.

EXAMPLE 9

1-[2-[2-(Anilinomethyl)-2-imidazolin-1-yl]-ethyl]-3-(3-trifluoromethylphenyl)-urea with a melting point of 128°–130° is obtained from 21.4 g of 1-aminomethyl-2-(anilinomethyl)-2-imidazoline and 18.7 g of m-trifluoromethylphenyl isocyanate in a manner analogous to that described under 2 (a).

EXAMPLE 10

1-[2-[2-(2-Chloroanilinomethyl)-2-imidazolin-1-yl]-ethyl]-3-(4-chlorophenyl)-urea with a melting point of 77°–80° is obtained from 22.4 g of 1-aminoethyl-2-(2-chlorophenyl)-2-imidazoline and 15.4 g of 4-chlorophenyl isocyanate in a manner analogous to that described under 2 (a).

The hydrochloride prepared therefrom melts at a temperature of 121°.

EXAMPLE 11

1-[2-[2-(4-Chloroanilinomethyl)-2-imidazolin-1-yl]-ethyl]-3-(4-tolyl)-urea with a melting point of 176°–179° is obtained from 25.3 g of 1-aminoethyl-2-(4-chloroanilinomethyl)-2-imidazoline and 13.3 g of p-tolyl isocyanate in a manner analogous to that described under Example 1 (a).

The hydrochloride prepared therefrom melts at a temperature of 113°.

EXAMPLE 12

(a) 1-[2-[2-(2,6-Dimethylanilinomethyl)-2-imidazolin-1-yl]-ethyl]-3-(4-tolyl)-urea is obtained from 26.1 g of 1-aminoethyl-2-(2,6-dimethylanilinomethyl)-2-imidazoline and 15.6 g of p-tolyl isocyanate in a manner analogous to that described under 1 (a) and this product is purified by the dihydrochloride in the following manner: the free base obtained as the residue is dissolved in ethyl acetate and two equivalents of 2.76 N alcoholic hydrochloric acid are added. The dihydrochloride is precipitated with ether and is obtained as an oil. After decanting off the solvent, the residue is dissolved in about 50 ml of isopropanol and again precipitated with about 1,000 ml of ether. After repeating this procedure again, the dihydrochloride is obtained only as a semi-crystalline product which does not have any definite melting point (foaming).

(b) The starting material required for the reaction, i.e. 1-aminoethyl-2-(2,6-dimethylanilinomethyl)-2-imidazoline, is prepared as follows:

48.0 g of 2,6-dimethylanilinoacetonitrile and 34.6 g of diethylenetriamine are heated in the presence of 300 mg of hydrogen sulfide gas until the evolution of ammonia has ceased. The resulting reaction mixture is taken up in benzene and the solvent and the starting materials are distilled off at 80°/0.1 mm Hg and the residue is purified via the dihydrochloride. The resulting 1-aminoethyl-2-(2,6-dimethylanilinomethyl))-2-imidazoline dihydrochloride melts at a temperature of 200°–203°. For the reaction, the base is liberated from the dihydrochloride in water and strong alkali.

EXAMPLE 13

(a) 1-[2-[2-Benzyl-2-imidazolin-1-yl]-ethyl]-3-(4-tolyl)-urea with a melting point of 149°–151° is obtained from 20.3 g of 1-aminoethyl-2-benzyl-2-imidazoline and 13.3 g of p-tolyl isocyanate in a manner analogous to that described under 2 (a). The hydrochloride melts at 155°–157°.

(b) The starting material required for the reaction, i.e. 1-aminoethyl-2-benzyl-2-imidazoline, is prepared in the following manner:

58.6 of benzyl cyanide and 57.9 g of diethylenetriamine are heated in the presence of 300 mg of hydrogen sulfide gas for 6 hours at 115°. The reaction mixture is taken up in 100 ml of benzene and extracted in portions with a total of 500 ml of cold 2 N hydrochloric acid. The hydrochloric acid solution is then poured into 500 ml of 10 N sodium hydroxide solution and the solution mixture is extracted with methylene chloride. The methylene chloride extract is distilled in vacuo, 1-aminoethyl-2-benzyl-2-imidazoline having a boiling point of 135°–142° under 0.03 mm Hg.

EXAMPLE 14

(a) 32.5 g of 1-aminoethyl-2-(2-hydroxyphenyl)-2-imidazoline are dissolved in 200 ml of toluene and 20.0 g of p-tolyl isocyanate in 75 ml of toluene are added dropwise at 20°–26°. The mixture, from which an oily phase separates out, is stirred for 3 hours at 90° and evaporated to the maximum possible extent in vacuo, the residue is dissolved in 100 ml of acetone and 60 ml of alcoholic hydrochloric acid (2.08 N) are added. 100 ml of absolute ether are added and the solution is left to crystallise. The 1-[2-[2-(2-hydroxyphenyl)-2-imidazolinyl]-ethyl]-3-(4-tolyl)-urea hydrochloride which is isolated and washed with isopropanol/acetone melts at 115° (decomposition).

(b) The starting material required for the reaction, i.e. 1-aminoethyl-2-(2-hydroxyphenyl)-2-imidazoline, is prepared as follows:

66.5 g of 2-methoxybenzonitrile and 56.75 g of diethylenetriamine are stirred with 500 mg of carbon disulphide for 8 hours in a bath at an external temperature of 130°. After the evolution of gas has ceased, the reaction mixture is taken up in toluene, the latter is evaporated, together with unconverted diethylenetriamine, in vacuo with rotation and the residue is distilled under a high vacuum; boiling point: 145°–150°/0.02 mm Hg or 135°/0.01 mm Hg. The compound is soluble in water and cannot be precipitated with concentrated sodium hydroxide solution. During the reaction, the methoxy group has been split to give the hydroxyl group and 1-aminoethyl-2-(2-hydroxyphenyl)-2-imidazoline has thus been obtained.

EXAMPLE 15

(a) 21.9 g of 1-aminoethyl-2-(4-methoxyphenyl)-2-imidazoline are initially introduced into 100 ml of toluene and, in the manner described in Example 2, with 13.3 g of p-tolyl isocyanate in 75 ml of toluene 1-[2-[2-(4-methoxyphenyl)-2-imidazolinyl]-ethyl]-3-(4-tolyl)-urea with a melting point of 66°–70° (from ethyl acetate/ether) is obtained. It contains water of crystallisation and is again recrystallised from ethyl acetate, after which the melting point of the anhydrous base is obtained: 134°–136°.

The salts are mostly hygroscopic or contain water of crystallisation and have a very low melting point. The hydrochloride crystallises in platelets from concentrated aqueous solution which contains 1 equivalent of hydrochloric acid.

(b) The starting material required for the reaction, i.e. 1-aminoethyl-2-(4-methoxyphenyl)-2-imidazoline is obtained analogously to Examples 2 and 14 from 39.9 g of 4-methoxybenzonitrile and 34.0 g of diethylenetriamine and 0.5 ml of carbon disulphide at 110°. Subsequent distillation gives 1-aminoethyl-2-(4-methoxyphenyl)-2-imidazoline with a boiling point of 144°–147°/0.04 mm Hg. The p-methoxy group is not split to the p-hydroxyl group.

EXAMPLE 16

(a) 19.0 g of 1-aminoethyl-2-(4-pyridyl)-2-imidazoline and 13.3 g of p-tolyl isocyanate are reacted as in Examples 2 and 15. By adding 200 ml of ethyl acetate after the reaction has ended, 1-[2-[2-(4-pyridyl)-2-imidazolinyl]-ethyl]-3-(4-tolyl)-urea is precipitated in the form of crystals. After separating off, the resulting product is recrystallised from ethyl acetate; melting point 109°–111°.

(b) The starting material required for the reaction, i.e. 1-aminoethyl-2-(4-pyridyl)-2-imidazoline, is obtained analogously to Examples 2 and 15 from 52 g of 4-cyanopyridine and 56.75 g of diethylenetriamine in the presence of 1 ml of carbon disulphide as the catalyst, by a slightly exothermic reaction; oil bath 110°, boiling point 130°–132°/0.015 mm Hg.

EXAMPLE 17

(a) 19.0 g of 1-aminoethyl-2-(2-pyridyl)-2-imidazoline and 13.3 g of p-tolyl isocyanate are subjected to a condensation reaction in toluene as the solvent, as in Examples 2 and 16. The product which crystallises during the reaction is filtered off with suction after 3 hours and recrystallised from 400 ml of ethyl acetate. The resulting 1-[2-[2-(2-pyridyl)-2-imidazolinyl]-ethyl]-3-(4-tolyl)-urea melts at 165°–167°.

A crystalline monohydrochloride with a melting point of 193°–195° is obtained from alcoholic solution with one equivalent of alcoholic 2.6 N hydrochloric acid on the addition of ethyl acetate.

(b) The starting material required, i.e. 1-aminoethyl-2-(2-pyridyl)-2-imidazoline, is obtained analogously to Example 16 from 52 g of 2-cyanopyridine, 56.75 g of diethylenetriamine and 1 ml of carbon disulphide, with stirring at 110° (bath temperature) and direct distillation of the crude product; boiling point 124°–127/0.04 mm Hg.

EXAMPLE 18

22.4 g of 1-aminoethyl-2(2-chlorophenyl)-2-imidazoline (obtained according to Example 2 (b)) are initially introduced into 100 ml of toluene and, at 20°–30°, 15.4 g of p-methylbenzoyl chloride in 100 ml of toluene are added slowly dropwise. A suspension forms and this is kept at 90° (bath temperature) for 3 hours and then cooled. After 12 hours, the oil which has separated out has crystallised completely. The crystalline fraction was purified as follows: it is dissolved in 200 ml of water, the turbid solution is filtered through Celite and the base is precipitated with saturated potassium carbonate solution and taken up in methylene chloride. After drying and evaporating in vacuo, the methylene chloride solution yields a viscous oil and this is dissolved in 50 ml of ethyl acetate and 32.5 ml of 2.65 N alcoholic HCl are added. The solution is substantially evaporated and the residue is dissolved in 200 ml of acetone, whereupon crystallisation takes place. The precipitate is filtered off with suction and washed with acetone and 1-[2-[4-methyl-benzoylamino)-ethyl]-2-(2-chlorophenyl)-2-imidazoline hydrochloride with a melting point of 100° (decomposition is thus obtained. It contains water of crystallisation and after prolonged drying under a high vacuum melts at 120°.

EXAMPLE 19

67.2 g of 1-aminoethyl-2-(2-chlorophenyl)-2-imidazoline (obtained according to Example 2 (b) are dissolved in 400 ml of toluene and, at room temperature, 57.3 g of ethyl p-isocyanato-benzoate in 150 ml of toluene are added dropwise. The reaction is brought to completion by stirring for 3 hours at 90° (bath temperature). The toluene solution is decanted off from the oil which has separated out and the latter is washed with toluene and then taken up in methylene chloride and the methylene chloride solution is washed with water and evaporated on a rotary evaporator. The residue is dissolved in 200 ml of ethyl acetate and 126 ml of 2.37 N alcoholic hydrochloric acid are added. On adding 500 ml of ethyl acetate, 1-[2-[2-(2-chlorophenyl)-2-imidazolin-1-yl]-ethyl]-3-(4-ethoxycarbonylphenyl)-urea hydrochloride crystallises and after recrystallisation from isopropanol/acetone this melts above 110°, with slow decomposition and foaming at 140°.

EXAMPLE 20

22.6 g of the 1-[2-[2-(2-chlorophenyl)-2-imidazolin-1-yl]-ethyl]-3-(4-ethoxycarbonyl-phenyl)-urea hydrochloride obtained according to Example 19 are dissolved in 900 ml of 95% alcohol and the base is liberated with 50 ml of 1 N sodium hydroxide solution. After adding 200 ml of 2 N sodium hydroxide solution, the mixture is stirred overnight. It is then neutralised with 200 ml of 2 N hydrochloric acid and slightly acidified with 51 ml of 1 N hydrochloric acid. The resulting mixture is evaporated to dryness in a rotary evaporator and the residue is twice boiled thoroughly with 100 ml of alcohol. The residue consists of sodium chloride; after substantial concentration, the solution yields crystalline 1-[2-[2-(2-chlorophenyl)-2-imidazolin-1-yl]-ethyl]-3-(4-carboxyphenyl)-urea hydrochloride, which is recrystallised from methanol/isopropanol and then melts at 240°–242° with decomposition.

EXAMPLE 21

16.8 g of 1-aminoethyl-2-(2-pyridyl)-2-imidazoline (prepared according to Example 17 (b)) in 100 ml of toluene and 16.9 g of ethyl 4-isocyanato-benzoate in 50 ml of toluene are subjected to a condensation reaction as in Example 19. 1-[2-[2-(2-Pyridyl)-2-imidazolin-1-yl]-ethyl]-3-(4-ethoxycarbonylphenyl)-urea, which is obtained as crystals, melts at 152°-154°. It is converted to the maleate, which has a melting point of 95°-97° with decomposition, by the method of Example 1 (a).

EXAMPLE 22

373 g of 1-aminoethyl-2-(4-pyridyl)-2-imidazoline (prepared analogously to Example 17 (b)) with a boiling point of 130°-132°/0.015 mm Hg are dissolved in 2 l of toluene and, at 20°-26°, 375 g of ethyl 4-isocyanatobenzoate in 1 l of toluene are added dropwise with vigorous stirring. An oily precipitate forms and this becomes crystalline after a further 3 hours reaction time at a temperature of 90°. The suspension is filtered with suction and the product is washed with toluene and ether and dried. 681 g of 1-[2-[2-(4-pyridyl)-2-imidazolin-1-yl]-ethyl]-3-(4-ethoxycarbonyl-phenyl)-urea with a melting point of 120° are obtained. The dihydrochloride is obtained from acetone by reaction with 2 equivalents of alcoholic hydrochloric acid.

EXAMPLE 23

(a) 68.1 g of 1-[2-[2-(4-pyridyl)-2-imidazolin-1-yl]-ethyl]-3-(4-ethoxycarbonyl-phenyl)-urea are dissolved in 1.3 l of 95% ethanol, 0.3 l of 2.3 N sodium hydroxide solution are added and the mixture is then stirred for 15 hours at room temperature. The equivalent amount (42.0 g) of glacial acetic acid is added to the alkaline solution and the clear solution is concentrated in vacuo to about ⅓ its volume. The crystalline precipitate thus obtained is isolated and washed with water and isopropanol. The resulting 1-[2-[2-(4-pyridyl)-2-imidazolin-1-yl]-ethyl]-3-(4-carboxy-phenyl)-urea melts at 181°-184° with decomposition.

(b) The hydrochloride is prepared as follows: 42.9 g of the base obtained above are suspended in a mixture of 0.1 l of methanol and 0.1 l of water and 1 equivalent of 2.4 N alcoholic hydrochloric acid is added. The resulting solution is filtered and concentrated in vacuo to about ⅓ its volume, whereupon a crystalline precipitate is obtained. Crystallisation is brought to completion by adding 0.1 l of isopropanol. The resulting hydrochloride melts at 217° with decomposition.

EXAMPLE 24

The 1-[2-[2-(2-pyridyl)-2-imidazolin-1-yl]-ethyl]-3-(4-ethoxycarbonyl-phenyl)-urea obtained according to Example 21 is saponified in the same way as described in Example 23 and 1-(2-[2-(2-pyridyl)-2-imidazolin-1-yl]-ethyl]-3-(4-carboxy-phenyl)-urea is obtained melting point 220°-223°. The resulting hydrochloride melts at 238°-240° with decomposition.

EXAMPLE 25

22.4 g of 1-aminoethyl-2-(2-chlorophenyl)-2-imidazoline are dissolved in 150 ml of toluene and 13.5 g of phenyl isothiocyanate in 75 ml of toluene are added dropwise. An oily precipitate separates out. The reaction mixture is stirred for 3 hours at 90° and cooled, the toluene is separated off from the precipitate and the residual oil is dissolved in methylene chloride and the methylene chloride solution is washed in water. An oil is obtained as the residue from the methylene chloride and after purification by chromatography on silica gel (450 g, solvent: acetone), this oil yields 1-[2-[2-(2-chlorophenyl)-2-imidazolin-1-yl]-ethyl]-3-phenylthiourea. The acid oxalate is obtained in crystalline form from the base in alcoholic solution with alcoholic oxalic acid and melts at 142° with decomposition.

The base can be obtained in crystalline form from the resulting oxalate by reaction with 2 N sodium hydroxide solution and is converted to the hydrochloride in acetone solution by reaction with the calculated amount of alcoholic 2.5 N hydrochloric acid. On concentrating the reaction solution and adding tetrahydrofuran, the hydrochloride is obtained as crystals and melts with 0.5 mol of water of crystallisation at 93°.

EXAMPLE 26

(a) 29.1 g of 1-(3-aminopropyl)-2-(4-pyridyl)-1,4,5,6-tetrahydropyrimidine are dissolved in 150 ml of toluene and 25.5 g of ethyl 4-isocyanato-benzoate in 100 ml of toluene are added slowly. An oily precipitate forms. The mixture is stirred at 90° for 3 hours, the toluene is decanted off and the resulting oil is dissolved in methylene chloride, the methylene chloride solution is filtered and the solvent is removed in vacuo. The oil, which is obtained in quantitative yield and crystallises very slowly, is saponified direct. The saponification is carried out in alcoholic solution with sodium hydroxide solution at room temperature. The alkaline solution is neutralised with glacial acetic acid and then substantially concentrated in vacuo. On cooling, 1-[3-[2-(4-pyridyl)-1,4,5,6-tetrahydropyrimidin-1-yl]-propyl]-3-(4-carboxyphenyl)-urea crystallises out and this melts at 262° with decomposition. The hydrochloride is obtained for example by reacting 16.2 g of the base in hot isopropanol with 17.9 ml of 2.26 N alcoholic hydrochloric acid. The resulting crystalline solid contains solvent and melts at 123° C. with decomposition. The solvent-free substance is obtained by heating in a high vacuum.

(b) The 1-(3-aminopropyl)-2-(4-pyridyl)-1,4,5,6-tetrahydropyrimidine used as the starting material is obtained analogously to Example 16 (b) from 26 g of 4-cyanopyridine, 36 g of dipropylenetriamine and 0.5 ml of carbon disulfide as the catalyst, by heating in an oil bath at 110°, and boils at a temperature of 154°-155°/0.015 mm Hg.

EXAMPLE 27

22 g of 2-chloro-benzimidoethyl ether hydrochloride (obtained from 2-chlorobenzonitrile and one equivalent of ethyl alcohol in chloroform and by saturation of the resulting solution with gaseous hydrochloric acid) and 23.6 g of 1-[1-(aminoethyl-(2)-amino)]-ethyl-(2)-3-(p-tolyl)-urea (obtained by the slow dropwise addition of 1 mole of p-tolyl isocyanate to a solution of 3 moles of diethylene triamine in toluene) are heated under reflux to the boil until the evolution of ammonia is complete. The alcoholic solution is concentrated to a small volume and treated with a mixture of acetone/ethyl acetate (1:1) in small portions and triturated, affording the crystalline hydrochloride of 1-[2-[2-(2-chlorophenyl)-2-imidazolin-1-yl]-ethyl]-3-(p-tolyl)-urea with a melting point of 108° C. The base which is set free by potassium carbonate melts at 166°-168° C.

EXAMPLE 28

(a) 27.7 g of ethyl 4-isocyanatobenzoate in 100 ml of ethyl acetate are added dropwise at 20°–24° C. to 34.4 g of 1-aminoethyl-2-[2,6-dimethyl-4-pyrimidinyl)-amino]-2-imidazoline. The solution, from which crystals gradually precipitate, is stirred for 3 hours at a bath temperature of 80° C. The crystals are collected by suction and washed with ethyl acetate, affording 1-[2-[2-(N-2,6-dimethyl-4-pyrimidinyl)-N-(4-ethoxycarbonylphenyl-carbamoylamino)-2-imidazolin-1-yl]-3-ethyl]-(4-ethoxycarbonylphenyl)-urea with a melting point of 168°–171° C. The residual mother liquor is concentrated in vacuo, and the residue is stirred in 300 ml of 1 N hydrochloric acid. The hydrochloric acid is then diluted with the same volume of water. Undissolved solid is decanted off and the turbid solution is clarified by filtration over activated charcoal. The filtrate is neutralised with 150 ml of potassium carbonate and the alkaline solution is repeatedly extracted with chloroform. The chloroform extract is worked up in the conventional manner, affording 1-[2-[2-(2,6-dimethyl-4-pyrimidinyl-amino)-2-imidazolidin-1-yl]-ethyl]-3-(4-ethoxycarbonylphenyl)-urea in the form of a viscous resin. This resin is dissolved in 200 ml of acetone and neutralised with 49 ml of ethanolic 2.4 N hydrochloric acid. Crystallisation commences after the addition of about 100 ml of ethyl acetate. The resulting 1-[2-[2-(2,6-dimethyl-4-pyrimidinyl-amino)-2-imidazolin-1-yl]-ethyl]-3-(4-ethoxycarbonylphenyl)-urea hydrochloride is isolated and washed with ethyl acetate. Melting point: 218°–220° C.

The 1-aminoethyl-2[(2,6-dimethyl-4-pyrimidinyl)-amino]-2-imidazoline used as starting material is obtained as follows:

(b) 24.6 g of 4-amino-2,6-dimethyl pyrimidine and 26.3 g of ethoxycarbonylisothiocyanate are stirred for 40 minutes under reflux in 100 ml of chloroform. After recrystallisation from 90% alcohol, the 3-ethoxycarbonyl-1-(2,6-dimethyl-4-pyrimidinyl)-thiourea crystals melt at 162°–165° C.

(c) 36 g of the ethoxycarbonylthiourea obtained in (b) are refluxed, with stirring, in 200 ml of 1 N sodium hydroxide for 1 hour. The precipitated crystals of 1-(2,6-dimethyl-4-pyrimidinyl)-thiourea melt at 236°–238° C.

(d) 20.4 g of the thiourea obtained in (c) and 16.7 g of methyl iodide are refluxed, with stirring, in 130 ml of methanol for 1 hour, affording 1-(2,6-dimethyl-4-pyrimidinyl)-S-methylisothiuronium iodide with a melting point of 196°–200° C. in quantitative yield.

(e) With stirring, 96 g of the isothiuronium salt obtained in (d) and 61 g of diethyl triamine are refluxed for 6 hours in 600 ml of methanol. Methyl mercaptan and ammonia are split off. The solution is concentrated to dryness and the residue is dissolved in 300 ml of water. The turbid solution is filtered clear and extracted exhaustively (i.e. 7 times) with chloroform. The extract yields 1-aminoethyl-2-[(2,6-dimethyl-4-pyrimidinyl)-amino]-2-imidazoline in the form of a yellow oil, which is purified via its dihydrochloride with a melting point of 208°–214° C.

EXAMPLE 29

The 1-[2-[2-(2,6-dimethyl-4-pyrimidinyl-amino)-2-imidazolin-1-yl]-ethyl]-3-(4-ethoxycarbonylphenyl)-urea obtained in Example 28 is saponified in the same manner as described in Example 23, affording 1-[2-[2-(2,6-dimethyl-4-pyrimidinyl-amino)-2-imidazolin-1-yl]-ethyl]-3-(4-carboxyphenyl)-urea with a melting point of 160° C. (decomposition at 180° C.). The hydrochloride melts at 239°–240° C. (with decomposition).

EXAMPLE 30

1-Aminoethyl-2-(2-pyridylamino)-2-imidazolin is reacted in ethyl acetate with ethyl-4-isocyanatobenzoate in the same manner as described in Example 28, affording crystalline 1-[2-[2-(2-pyridylamino)-2-imidazolin-1-yl]-ethyl]-3-(4-ethoxycarbonylphenyl)-urea.

EXAMPLE 31

In accordance with the procedure described in Example 22, 1-aminoethyl-2(3-pyridylmethyl)-2-imidazoline is obtained from 3-(cyanomethyl)-pyridine and reacted with ethyl 4-isocyanatobenzoate, affording 1-[2-[2-(3-pyridylmethyl)-2-imidazolin-1-yl]-ethyl]-3-(4-ethoxycarbonylphenyl)-urea with a melting point of 158.8° C. The dihydrochloride melts at 210° C. (with decomposition).

EXAMPLE 32

The ethyl ester obtained in Example 31 is saponified in the same manner as described in Examples 23 and 29, affording 1-[2-[2-(3-pyridylmethyl)-2-imidazolin-1-yl]-ethyl]-3-(4-carboxyphenyl)-urea.

What is claimed is:

1. A urea or amido compound of the formula

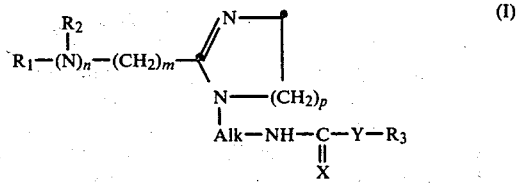

in which $R_1$ is pyridyl or pyridyl substituted by a group selected from halogen, lower alkyl, lower alkoxy, alkoxycarbonyl, carboxyl and trifluoromethyl and $R_3$ is phenyl or phenyl substituted by a group selected from halogen, lower alkyl, lower alkoxy, power alkoxycarbonyl, carboxyl and trifluoromethyl, $R_2$ is hydrogen or lower alkyl, n is 0 or 1, m is 0 or 1, p is 1, Alk is a lower alkylene radical with 2–3 carbon atoms in the linear chain, X is oxygen or sulphur and Y an imino group or a direct bond, and therapeutically acceptable salts thereof.

2. A compound as claimed in claim 1, corresponding to formula I, in which $R_1$ is pyridyl-2, pyridyl-4, or pyridyl-2 or pyridyl-4 substituted by a group selected from halogen, lower alkyl, lower alkoxy, lower alkoxycarbonyl, carboxyl and trifluoromethyl and $R_3$ is phenyl or phenyl substituted by a group selected from halogen, lower alkyl, lower alkoxy, alkoxycarbonyl, carboxyl and trifluoromethyl, n is 0 or 1, m is 0 or 1, p is 1, provided that if m is 0, n is 0, $R_2$ is hydrogen, Alk is a lower alkylene radical with 2 carbon atoms in the linear chain, X is oxygen and Y an imino group and therapeutically acceptable salts thereof.

3. A compound as claimed in claim 1, corresponding to formula I, in which $R_1$ is pyridyl-2, pyridyl-4, or pyridyl-2 or pyridyl-4 which is substituted by a group selected from halogen, lower alkyl, carboxyl or trifluoromethyl, $R_3$ is phenyl or phenyl substituted by a group selected from halogen, lower alkyl, carboxyl or trifluoromethyl, n is 0 or 1, m is 0 or 1, p is 1, provided that if m is 0, n is 0, $R_2$ is hydrogen, Alk is a 1,2-ethylene radical, X is oxygen and Y an imino group and therapeutically acceptable salts thereof.

4. A compound as claimed in claim 1, corresponding to formula I, in which $R_1$ is pyridyl-2, pyridyl-4, or pyridyl-2 or pyridyl-4 substituted by a group selected from chlorine, methyl, carboxyl and trifluoromethyl, $R_3$ is phenyl or phenyl substituted by a group selected from chlorine, methyl, carboxyl and trifluoromethyl, n is 0 or 1, m is 0 or 1, p is 1, provided that if m is 0, n is 0, $R_2$ is hydrogen, Alk is a 1,2-ethylene radical, X is oxygen and Y an imino group and therapeutically acceptable salts thereof.

5. A compound as claimed in claim 1 and being 1-[2-[2-(4-pyridyl)-2-imidazolin-1-yl]-ethyl]-3-(4-carboxyphenyl)-urea and a therapeutically useful salt thereof.

6. A compound as claimed in claim 1 and being 1-[2-[2-(2-pyridyl)-2-imidazolin-1-yl]-ethyl]-3-(4-carboxyphenyl)-urea and a therapeutically useful salt thereof.

* * * * *

UNITED STATES PATENT AND TRADEMARK OFFICE
CERTIFICATE OF CORRECTION

PATENT NO. : 4,292,429
DATED : September 29, 1981
INVENTOR(S) : ADRIAN MARXER

It is certified that error appears in the above-identified patent and that said Letters Patent are hereby corrected as shown below:

Claim 1, Column 16, Line 44 reads:

"halogen, lower alkyl, lower alkoxy, power alkoxycar-"

Should read:

-- halogen, lower alkyl, lower alkoxy, lower alkoxycar- --

Signed and Sealed this

Twenty-eighth Day of June 1983

[SEAL]

Attest:

GERALD J. MOSSINGHOFF

Attesting Officer

Commissioner of Patents and Trademarks